United States Patent
Reed et al.

(10) Patent No.: US 9,926,589 B2
(45) Date of Patent: Mar. 27, 2018

(54) IDENTIFICATION AND QUANTIFICATION OF MULTIPLE NUCLEIC ACID TARGETS IN COMPLEX MIXTURES

(71) Applicant: VIRGINIA COMMONWEALTH UNIVERSITY

(72) Inventors: Jason Reed, Richmond, VA (US); Andrey Mikheykin, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 15/022,582

(22) PCT Filed: Sep. 11, 2014

(86) PCT No.: PCT/US2014/055056
§ 371 (c)(1),
(2) Date: Mar. 17, 2016

(87) PCT Pub. No.: WO2015/041910
PCT Pub. Date: Mar. 26, 2015

(65) Prior Publication Data
US 2016/0230211 A1 Aug. 11, 2016

Related U.S. Application Data

(60) Provisional application No. 61/879,306, filed on Sep. 18, 2013.

(51) Int. Cl.
*C12Q 1/68* (2006.01)

(52) U.S. Cl.
CPC .......... *C12Q 1/6806* (2013.01); *C12Q 1/686* (2013.01)

(58) Field of Classification Search
None
See application file for complete search history.

(56) References Cited

PUBLICATIONS

Pemov et al (2005 Nucleic Acids Research vol. 33 No. 2 e11 9 pp).*
FastScan AFM brochure from Bruker (public availability date May 2, 2011).*
Edwards et al (1994 Genome Research 3:S65-S75).*
Fang et al., "Solid-state DNA sizing by atomic force microscopy", Analytical Chemistry, 1998, pp. 2123-2129, vol. 70, No. 10.
Limanskii, "Visualization of amplicons after polymerase chain reaction", Biophysics, 2005, pp. 45-49, vol. 50, No. 6.
Reed et al., "Identifying individual DNA species in a complex mixture by precisely measuring the spacing between nicking restriction enzymes with atomic force microscope", Journal of the Royal Society Interface, 2012, pp. 2341-2350, vol. 9, No. 74.
Tanigawa et al., "Detection and mapping of mismatched base pairs in DNA molecules by atomic force microscopy", Nucleic Acids Research, 2000, pp. i-v, vol. 29, No. 9.
Woolley et al., "Direct haplotyping of kilobase-size DNA using carbon nanotube probes", Nature Biotechnology, 2000, pp. 760-763, vol. 18, No. 7.
Mikheikin et al., "Atomic force microscopic detection enabling multiplexed low-cycle-number quantitative polymerase chain reaction for biomarker assays", Analytical Chemistry, 2014, pp. 6180-6183, vol. 86, No. 13.

* cited by examiner

*Primary Examiner* — Christopher M Gross
(74) *Attorney, Agent, or Firm* — Whitham, Curtis & Cook

(57) ABSTRACT

A complex mixture is analyzed for multiple nucleic acid sequences (e.g., DNA or RNA sequences) simultaneously by target specific multiplex amplification followed by single molecule detection of amplicons by Atomic Force Microscopy (AFM). The presence or absence of target nucleic acids can be determined from the presence or absence of specific amplicons for those nucleic acids. In addition, quantification of target nucleic acids in the complex mixture is achieved by determination of the numbers of amplicons.

6 Claims, 6 Drawing Sheets

IDENTIFICATION AND QUANTIFICATION OF MULTIPLE NUCLEIC ACID TARGETS IN COMPLEX MIXTURES

FIELD OF THE INVENTION

Embodiments of the invention relate to a highly sensitive technique to identify and quantify multiple nucleic acid targets in complex mixtures.

BACKGROUND OF THE INVENTION

High-throughput transcriptomic assays, such as microarrays or RNA-Seq, allow identification of gene expression signatures consisting of hundreds-to-thousands of genes. However, these high-throughput techniques are costly, time-consuming (turnaround time one-to-several days), need centralized processing in many cases, and are not very sensitive in terms of the amount of input material (Katagiri et al., 2009; Nagalakshmi et al., 2010). For example, the hybridization-based, nCounter® System requires ~100 ng of input total RNA for gene expression studies, with typical assay time 16 hrs (Kulkarni, 2011). In particular, assay sensitivity is becoming an important figure of merit as interest grows in studying minute quantity samples, such as needle biopsies, aspirates and circulating tumor cells (CTCs) (Powell et al., 2012), rather than bulk tissue (Eberwine et al., 2012; Dalerba et al., 2011; Bendall et al., 2012). At the same time, there is no need to use cost- and time-intensive high-throughput techniques in many situations where an assay of several-to-tens of genes will suffice, such as in the case of established biomarker panels (Habel et al., 2006; Colman et al., 2010; Garcia-Bilbao et al., 2012; Mizuarai et al., 2010).

Real-time polymerase chain reaction, also known as quantitative PCR (qPCR), is the golden standard for gene expression-based biomarker assays, due to its sensitivity (single-molecule in the ideal case) and broad dynamic range. However, traditional qPCR is difficult to multiplex, and as a result multi-target experiments require many single reactions to be conducted in parallel, either in microplate format or, in the case of limited-quantity samples, using pre-amplification and proprietary microfluidic platforms—both approaches which add substantial cost, time and complexity to the analysis (Stahlberg et al., 2011; Sanchez-Freire et al., 2012). Multiplexing standard PCR is problematic because target sequences are typically amplified non-uniformly, which results in misrepresentation of low-abundance and/or "difficult" amplicons due to the depletion of reagents (dNTP and primers) and inhibition of polymerase by amplicons (SantaLucia, 2007); another problem is off-target primer binding and primer dimer formation, for which the probability grows as the number of primer pairs in multiplex increases; note that both these effects accumulate over a reaction time course and result in artefacts at a high number of cycles.

SUMMARY OF THE INVENTION

Embodiments of the present invention fill the gap between low- (e.g. RT-qPCR) and high-throughput (e.g. microarrays) techniques. Embodiments of the invention allow for simple and effective multiplexing of targets in one qPCR reaction. In preferred embodiments, target-specific multiplex amplification of up to about ten targets with about 10 to 15 cycles of PCR is followed by single-molecule detection of amplicons with Atomic Force Microscopy (AFM), thus allowing for accurate identification and quantification of said targets.

The method of the present invention is applicable to virtually any analytical problem requiring sensitive identification or quantification of multiple nucleic acid targets. In some embodiments, the present invention is used for example in molecular diagnostics to quantify multiple nucleic acid targets including, but not limited to, gene expression, copy number variation, protein isoforms, gene translocation, microRNA, and other genetic variations at up to the single-cell level.

DETAILED DESCRIPTION OF THE INVENTION

Figure 1:
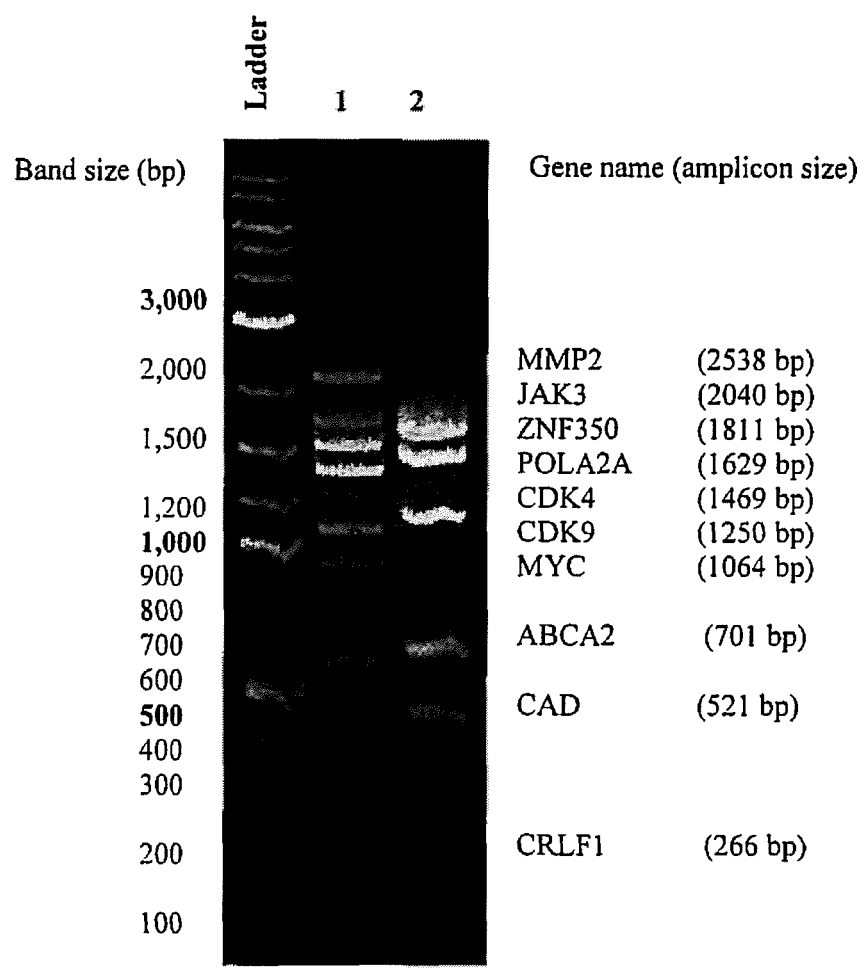
FIG. 1. Image of 10plex PCR products (30 amplification cycles) run on 1% agarose gel. cDNA obtained from Universal Total Human Reference RNA (Lane 1) or FirstChoice Human Brain Reference RNA (Lane 2) were used as templates. Ladder—2-Log DNA Ladder (New England Biolabs). Band sizes and genes names (along with corresponding amplicon sizes) are shown on the left and right sides of the gel image, respectively.

Novel scientific instruments are required to apply post-genomic era data in medicine and biotechnology. Embodiments of the present invention relate to highly-sensitive nanosensor-based techniques to identify and quantify multiple nucleic acid targets in complex mixtures.

Embodiments of the invention include methods for analyzing multiple nucleic acid targets in a complex mixture. Examples of the methods comprise the steps of:
i) performing a polymerase chain reaction (PCR) using primers which produce a uniquely sized amplicon for each of said targets;
ii) identifying individual amplicons using atomic force microscopy (AFM); and
iii) correlating identified amplicons with specific nucleic acid targets of said multiple nucleic acid targets.

In some embodiments, methods include quantifying specific nucleic acid targets in the complex mixture as a function of a total number of each individual amplicon identified. In some embodiments, amplicons are visualized on an agarose gel or other substrate. Preferred embodiments of the invention combine target-specific multiplex amplification through PCR with single-molecule amplicon detection using Atomic Force Microscopy (AFM). In other words, a practitioner is able to identify the nucleotide sequences present in a sample and determine the amounts of said sequences. Here, a nucleic acid target is a nucleic acid with a specific sequence to be tested for. Embodiments of the invention are applicable to both to a qualitative and a quantitative determination of the presence of a target nucleic acid in a complex mixture.

In the present invention, a complex mixture is defined as any sample containing a plurality of nucleic acid sequences that are amplified or to be amplified. In some embodiments, the sample may contain multiple genes or biomarkers in which a section of each gene's nucleic acid sequence is amplified. In other embodiments, the sample may contain a single gene or biomarker in which several sections of its nucleic acid sequence are amplified. In still other embodiments, the sample may contain multiple genes or biomarkers on multiple sequences for which one or more sections of each sequence are to be amplified. The complex mixture can be referred to as a nucleic acid sample, and can be any sample containing the nucleic acid(s), e.g. body fluid sample, tissue sample, blood sample, etc.

Examples of a nucleic acid sample include but are not limited to a biological sample collected from a plant, an animal, or the like; a sample prepared from a cultured cell lysate; or a nucleic acid solution extracted and purified from a biological sample. In some embodiments, human-derived biological samples to be used for clinical, forensic, or other tests and nucleic acid solutions extracted and purified from such human-derived biological samples are used. In addition, the nucleic acid sample may be directly used after the collection from an organism, or may be prepared before use. The preparation method is not specifically limited as long as DNA, RNA, or such a nucleic acid contained in the biological sample is not impaired, and a usual preparation method for biological samples can be applied. For example, DNA extracted and purified from a biological sample and amplified by PCR or like method, or cDNA synthesized from RNA contained in a biological sample with a reverse transcriptase can be used.

The polymerase chain reaction (PCR), is a means to amplify the amount of DNA or mRNA fragments, e.g. of a specific gene, in a sample. If mRNA fragments shall be amplified, they first have to be transcribed to cDNA in a reverse transcription (RT) step. In this case, the reaction is called RT-PCR.

Two primers specific for each nucleic acid target are used for the PCR and are about 5-60, or more preferably 10-50 nucleotides long. The forward and reverse primers are complementary to the sense and anti-sense strands of the nucleic acid target respectively.

In some embodiments, the number of PCR cycles is limited to avoid the differential amplification distortion present in normal qPCR, which in most cases requires 30+ amplification cycles. In an exemplary embodiment, the number of PCR cycles is limited to about 5 to 20, or more preferably about 10 to 15 cycles. It can be for example 10, 11, 12, 13, 14, or 15 cycles.

Amplicons can be distinguished by their sizes, and given the high sizing precision achievable with AFM, typically <3% relative error (CV) (Reed et al., 2012; Sundstrom et al., 2012), multiple targets can be discriminated simultaneously. In exemplary embodiments, the amplicons are longer than about 200 base pairs (bp) for easy visualization and have at least about 100 bp differences in size to easily distinguish them from each other. For example, in a multiplex reaction with ten target nucleic acids, some amplicons are 1000-2000 bp in length, which is significantly longer than those used in typical qPCR assays (100-150 bp).

Increasing the PCR extension time of the longer amplicons (1000-2000 bp) from 2.5 minutes, as recommended for amplicons of this size, up to 10 minutes significantly improves the PCR yield of these amplicons. In order to minimize primer-primer interactions and nonspecific primer binding to template, the primer concentrations should be as low as possible. In preferred embodiments, a primer concentration of about 20-200 nM, more preferably 20 nM, is used. A person of ordinary skill in the art would be able to optimize the primers in a singleplex reaction to identify the minimal working concentration. Primer pairs are used in the multiplex reactions at concentrations determined in singleplexes without further optimization Because individual amplicons are easily detected by AFM, the present invention has orders of magnitude higher sensitivity (1000×) compared to bulk fluorescent techniques such as microarray and capillary electrophoresis. Furthermore, in some embodiments, no fluorescent dyes or any other types of labeling are used, thus reducing the complexity and cost of the analysis. In some aspects of the invention, amplicons are visualized on an agarose gel (The amplicons from optimization may be visualized on an agarose gel or other substrate).

In preferred embodiments, the AFM has a high scan speed and is partially or fully automated. General purpose AFM instruments are commonly available in universities and other research institutions. High scan speed (imaging rate approaching 1 frame per second and beyond, rate of pixels per second greater than 1 million, and pixel sizes of 2×2 nm up to and including 100×100 nm). AFMs have been commercially available for several years and are beginning to replace "standard" AFMs in the installed base, and are often available in shared core facilities as are quantitative PCR machines and DNA sequencing instruments; the approximate retail price of a state of the art general purpose high speed AFM is on the order of the former and much less than the latter. If a commercially-available high scan rate AFM is used (e.g. Bruker FastScan or Asylum Cypher), the assay time is considerably reduced, e.g. to 1.4 hrs or less, which is of similar duration as regular 30-35 cycle qPCR, and significantly more rapid than existing hybridization-based detection schemes (14-16 hr). Embodiments of the present invention do not require many of the features present in a general purpose AFM, such as complex z-axis feedback control and electronics supporting multiple imaging modes (surface elasticity mapping, electric and magnetic imaging, etc.).

Figure 6:
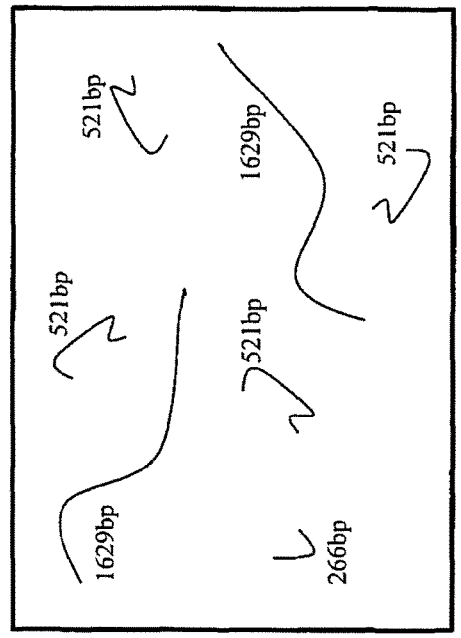
FIG. 6. A simplified example illustrating an embodiment of the invention in which the primers used for PCR produce amplicons that can be identified and quantitated by their unique size.

FIG. 6 provides a simple illustration of an embodiment of the invention. As shown in the table, four target nucleotide sequences, A-D, have been selected for amplification using specific pairs of primers. Each primer pair produces an amplicon of a unique size (e.g., the sizes of the amplicons from Targets A-D are each different in by numbers). After performing AFM, it is determined based on the sizes of the amplicons that targets A-C are present in the sample. However, target D is not present since no amplicons corresponding to 2538 bp are detected. After counting the amount of each uniquely sized amplicon present, one can determine that there is double the amount of target B as compared to C and double the amount of target A as compared to B.

Embodiments of the present invention are applicable to virtually any problem requiring identification of multiple nucleic acid targets in a complex mixture. In some embodiments, analysis of multiple nucleic acid targets can be used in several biological and biomedical applications, for example pathogen detection and identification as well as analysis of disease biomarkers in a patient sample. As an illustration, the type of pathogen infecting a salmon farm is identified with this technique by analyzing a tissue sample with primers against the nucleic acid sequence of multiple pathogens likely to be involved. In addition, the disease state of a patient may be more precisely identified by analyzing a plurality of disease biomarkers using the method of some embodiments of the invention. For example, the presence of biomarkers indicative of an increased risk of developing breast or other types of cancer can be identified using the techniques of the invention. Some aspects of the invention may be used to identify and separate genetically engineered crops from non-engineered crops using multiple markers. For example, embodiments of the present invention will be able to determine if a farmer's non-engineered crops have been contaminated by nearby engineered crops through the amplification of nucleic acid targets found solely in the engineered crops.

Another aspect of the present invention is applicable to virtually any analytical problem requiring sensitive measurement of concentrations of multiple nucleic acid targets. In some embodiments, quantification of multiple nucleic acid targets can be used in several biological and biomedical applications, for example gene expression quantification in cancer diagnostics, tumor profiling and drug design. Aside from transcriptional profiling, this technique could be used to quantify multiple nucleic acids targets in other assays where the molecular concentration is relevant, such as in studies of genomic copy number variation, mRNA isoform detection and analysis of chromosomal translocations.

The invention will be further illustrated by the following examples. However, these examples and figures should not be interpreted in any way as limiting the scope of the present invention.

Example

Materials & Methods

Chemicals:
Primers for multiplex PCR were design using Primer-BLAST software (Ye et al., 2012). Sequences for qPCR primers were taken from qPrimerDepot (Cui et al., 2007). All primers were ordered from IDT DNA Technology (Corallville, Iowa) and used without further purification. Universal Total Human Reference RNA (Stratagene, Agilent Technologies, Santa Clara, Calif.) solution was precipitated and re-suspended in RNAse-free water according to manufacturer's protocol, FirstChoice® Human Brain Reference RNA (Life Technologies, Carlsbad, Calif.) was used without purification. All RNA were aliquoted and stored at −80 C. New England Biolab's AMV LongAmp® Taq RT-PCR Kit was used for reverse transcription and multiplex PCR amplification with LongAmp® Taq 2× Master Mix included in the kit replaced by LongAmp® Hot Start Taq 2× Master Mix. 1-(3-aminopropyl)silatrane (APS) was a gift.

Multiplex RT-PCR:
Reverse transcription was conducted according to the manufacturer's protocol with 2 ug amount of total RNA per reaction tube. $(dT)_{23}VN$ primer included in kit was used for reverse transcription. Multiplex PCR was conducted according to the manufacturer's recommendation except the extension time was increased to 10 min. Primer annealing temperature was 60° C. For Bioanalyzer and AFM analysis 20 PCR tubes with the amount of cDNA corresponding to 50 ng of total RNA per tube were used for 15 cycles of PCR, combined after the reaction in one tube, purified twice with ZYMO Research DCC-5 columns and quantified with Qubit® fluorimetric assay. Typical yield was 800-1500 pg/micol in 20-50 microl elution volume. To check the quality of PCR products with 1% agarose gel, the amount of cDNA corresponding to 50 ng of total RNA was amplified (30 cycles) in one tube (FIG. 1).

Multiplex Primer Design and Optimization of Experimental Conditions:
Primers were designed using Primer-BLAST software with some constraints the same as for standard RT-qPCR: to avoid amplification of genomic DNA, primers were designed either to span exon-exon junctions or to be separated by at least one intron; primer binding sites do not contain known single nucleotide polymorphisms; all primer pairs have been checked against human genome and transcriptome databases for non-specific binding. There are also some specific requirements for amplicons to be analyzed by AFM imaging: the amplicons should be longer than about 200 bp to easily visualize them and have at least about 100 bp differences in size to distinguish them from each other. This means that, for example a tenplex, some amplicons should be 1000-2000 bp in length, which is significantly longer than those used in typical qPCR assays (100-150 bp). Analysis of the longest amplicon found that increasing the extension time from 2.5 minutes, as recommended by the kit's manufacturer for amplicons of this size, up to 10 minutes significantly improved the PCR yield of this amplicon. In order to minimize primer-primer interactions and nonspecific primer binding to template, the primer concentrations should be as low as possible. To optimize primer concentrations, 30 amplification cycles of singleplexes were conducted for all primer pairs at a primer concentration of 20 nM and the amplicons were visualized in a 1% agarose gel. It was found that most of primers work at this concentration. Other primers were taken at various concentrations up to 200 nM to identify the minimal working concentration. All primer pairs were used in the multiplex at concentrations determined in singleplexes without further optimization.

RT-qPCR:
The same transcription products were used as templates for qPCR. ABI Prism® 7900 Detection System (Applied Bioscience) was employed according to the manufacturer's protocol. SYBRGreen® chemistry was used to detect amplicons. qPCR was conducted at two annealing temperatures, 55° C. and 60° C., and good correspondence was found between these two datasets in most cases (see Table 1). For POLR2A gene, Ct values at 55° C. are shifted towards higher values probably due to primer dimer formation and/or secondary structures at this lower temperature; however, the brain/human reference ratio values are the same in both these cases.

TABLE 1 qPCR Ct values at primer annealing temperatures 55° C. and 60° C.

| Gene name | Universal Human | | FirstChoice Brain | | Brain/Human Ratio | |
|---|---|---|---|---|---|---|
| | 55° C. | 60° C. | 55° C. | 60° C. | 55° C. | 60° C. |
| ABCA2 | 29.0 | 29.2 | 26.5 | 27.4 | 5.76 | 3.43 |
| CAD | 23.3 | 23.2 | 27.2 | 28.0 | 0.07 | 0.04 |
| CDK4 | 19.2 | 19.3 | 23.2 | 24.1 | 0.06 | 0.04 |
| CDK9 | 23.0 | 22.9 | 23.3 | 23.3 | 0.83 | 0.37 |
| CRLF | 33.1 | 31.3 | 35.1 | 32.3 | 0.25 | 0.49 |
| JAK3 | 29.0 | 29.0 | 31.3 | 31.7 | 0.19 | 0.15 |
| MMP2 | 19.8 | 18.8 | 27.8 | 29.3 | <0.01 | <0.01 |
| MYC | 21.8 | 21.4 | 29.0 | 30.0 | 0.01 | <0.01 |
| POLR2A | 31.4 | 23.4 | 33.0 | 25.5 | 0.33 | 0.34 |
| ZNF350 | 25.7 | 25.6 | 26.3 | 26.5 | 0.69 | 0.51 |

Data represent average of two replicates for each sample. For replicates, the variance in Ct values was within the typical range for qPCR.

Bioanalyzer Assay:

1 microL of 800 pg/microL of each amplicon solution was used to run Agilent 2100 Bioanalyzer High Sensitivity DNA assay (Agilent Technologies) according to the manufacturer's protocol.

AFM Sample Preparation and Imaging:

Freshly cleaved mica was treated with 1-(3-aminopropyl) silatrane (APS) according to Shlyakhtenko et al. (2003), then rinsed with 5 microL of water. One microL of 10 pg/microL of amplicons was deposited on derivatized mica, incubated for 20 min at room temperature in a humidified environment, then rinsed with 3 ml of DI water. Images were acquired using a Bruker Dimension Icon AFM in 'soft' taping mode (RFESP cantilevers, 1-3 N/m spring constant) at a lateral speed of 0.02 mm/sec, and resolution of 2×2 nm per pixel. The double-stranded amplicon DNA can be distinguished from single stranded DNA and RNA by the shape and height (apparent height in AFM image 0.6 nm, apparent thickness 8-10 nm). A non-primer control was conducted at the standard experimental conditions and the abundance of DNA molecules is <1 per 10×10 micron AFM image.

AFM Data Processing:

Images were analyzed by an image processing program developed for this application, called AFMExplorer. Details of the image analysis procedure are given in Sundstrom et al. (2012). Briefly, AFM images are flattened and pre-filtered to reduce noise, followed by adaptive thresholding based on pixel height to recognize regions corresponding to DNA molecules; a binary skeletonization procedure is used to determine the best backbone contour for each molecule, and the molecule length in nanometers is calculated by a cubic spline fit to the backbone pixel set. The program is manually queued to ignore crossed molecules, otherwise the molecule identification and measurement is fully automatic. The relative dispersion (CV) in measured contour lengths for a population of like DNA molecules is better than +/−3% under these imaging conditions (Reed et al., 2012).

For the Bioanalyzer data, chromatogram peaks are associated with corresponding mRNA species by standard calibration; for AFM by expected amplicon length (AFM, 0.33 bp/nm [pitch of bDNA]). In the AFM experiments, counts for each target represent the sum of molecules detected with lengths equal to the expected amplicon length, +/−3%, which represents a conservative estimate of AFM sizing error (Reed et al., 2012). Relative abundances are calculated as the ratio (cnts brain)/(cnts hum ref) for each species. The qPCR abundances were calculated from the difference in threshold amplification cycle number (Ct value) between the samples. The number of amplicon molecules measured by AFM from the Human Reference and Brain total RNA samples is 2,535 (4.16 zeptomole) and 1,533 (2.55 zeptomole), respectively.

Technical Repeat Experiments:

Products of three individual amplification reactions were quantified with AFM to study reaction-to-reaction variability of the developed technique. Universal Human Reference cDNA was taken in the amount, corresponding to 50 ng of total RNA per PCR tube. PCR was conducted using a protocol described in the manuscript. The products from each PCR tube were purified with MinElute® Qiagen PCR CleanUp kit, dialyzed against deposition buffer and analyzed with AFM as described above. Note this scheme of this replicate experiment is different from one used to compare AFM-PCR to Bioanalyzer analysis and qPCR; in the latter case twenty PCR tubes were combined for comparison of AFM and Bioanalyzer quantification (necessary due to sensitivity limits of Bioanalyzer), and the PCR-induced variability is thus greatly reduced. Good reaction-to-reaction reproducibility allows for quantify gene expression without repeats in contrast to conventional qPCR where the results are usually obtained at least in triplicate or quadruplicate. This property of the PCR-AFM would be important in cases where the initial amount of nucleic acids is limited.

Results

Figure 5:
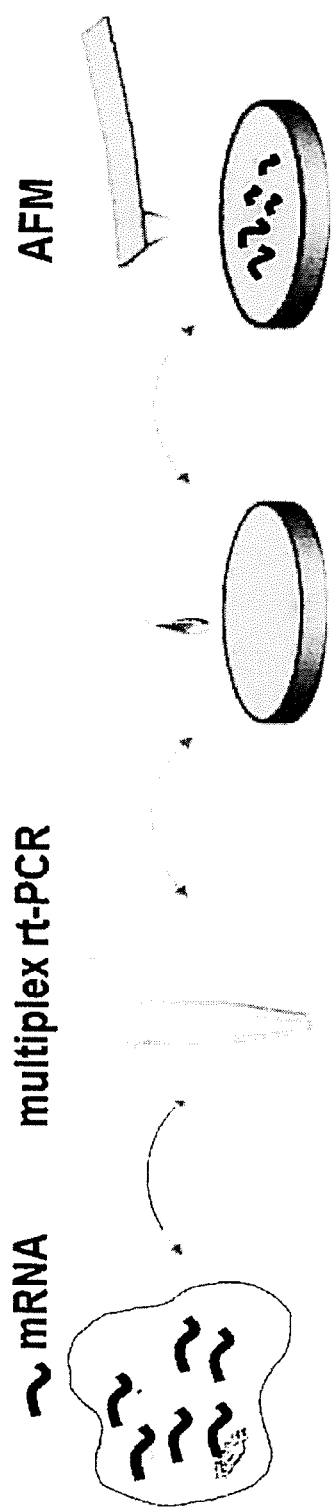
FIG. 5. A flow diagram illustrating the workflow of a preferred embodiment according to the present invention.

We demonstrate an embodiment of the present invention by measuring the relative expression level of ten human genes in two different total RNA samples, and find a high concordance between single-reaction multiplex PCR/AFM data and data obtained from panel of twenty independent singleplex qPCR assays. FIG. 5 illustrates the workflow of the present example. RNA samples isolated from cells were used in a multiplex RT-PCR reaction. The resulting DNA amplicons were placed on APS-treated mica surfaces for AFM imaging.

Multiplex PCR.

Figure 2:
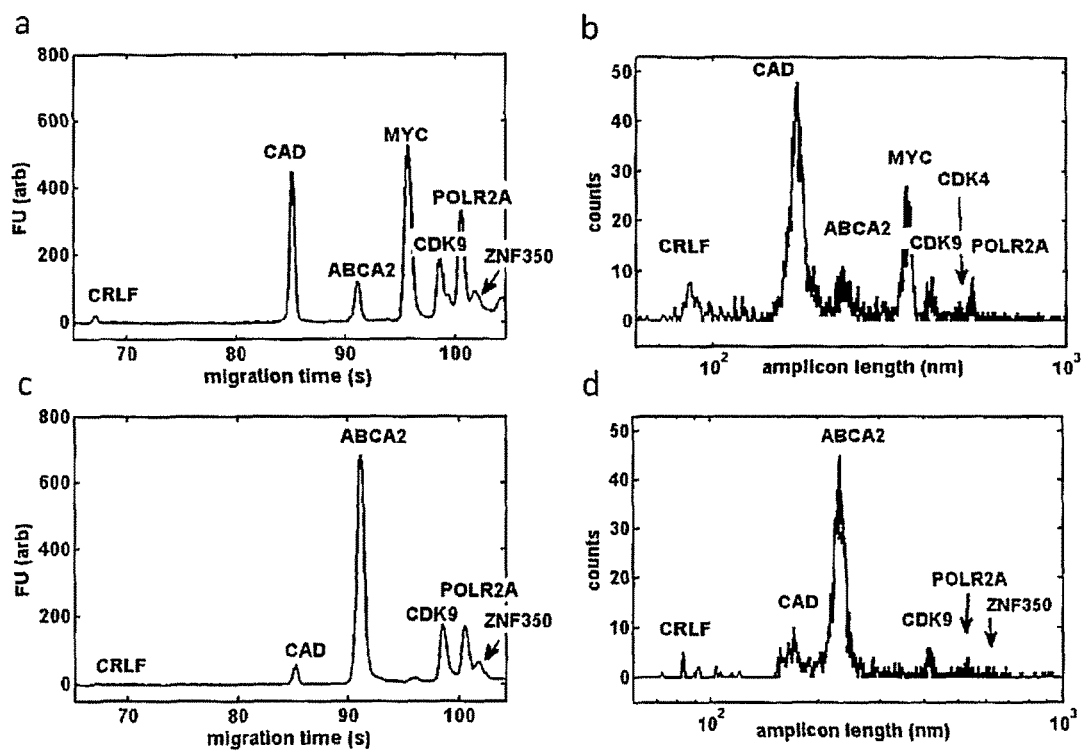
FIG. 2. (a) Bioanalyzer chromatogram of human reference total RNA 10-plex amplicons (1 uL, conc. 800 pg/uL) compared to (b) size distribution of amplicons measured with AFM (est. ~1 uL, conc. 10 pg/uL; 2,500 molecules). Note that the AFM-determined amplicon sizes are plotted on a logarithmic scale for comparison purposes. Human brain total RNA 10-plex measured by (c) bioanalyzer (800 pg/uL) and (d) AFM (10 pg/uL; 1500 molecules).

Ten human genes (see table 1) were chosen as a model biomarker panel; we measured the difference in expression of transcripts in this panel between two commercially available total RNA samples: Universal Total Human Reference RNA (Stratagene) and FirstChoice Human Brain Reference RNA (Life Technologies). To verify that all ten genes could be co-amplified in the same reaction, 30 cycles of multiplex RT-PCR were conducted using both total RNA samples, and separated in 1% agarose gel (FIG. 1). The Agilent Bioanalyzer DNA high-sensitivity kit was used to quantify the multiplex PCR after 15 amplification cycles (FIG. 2).

AFM Imaging.

Figure 3:
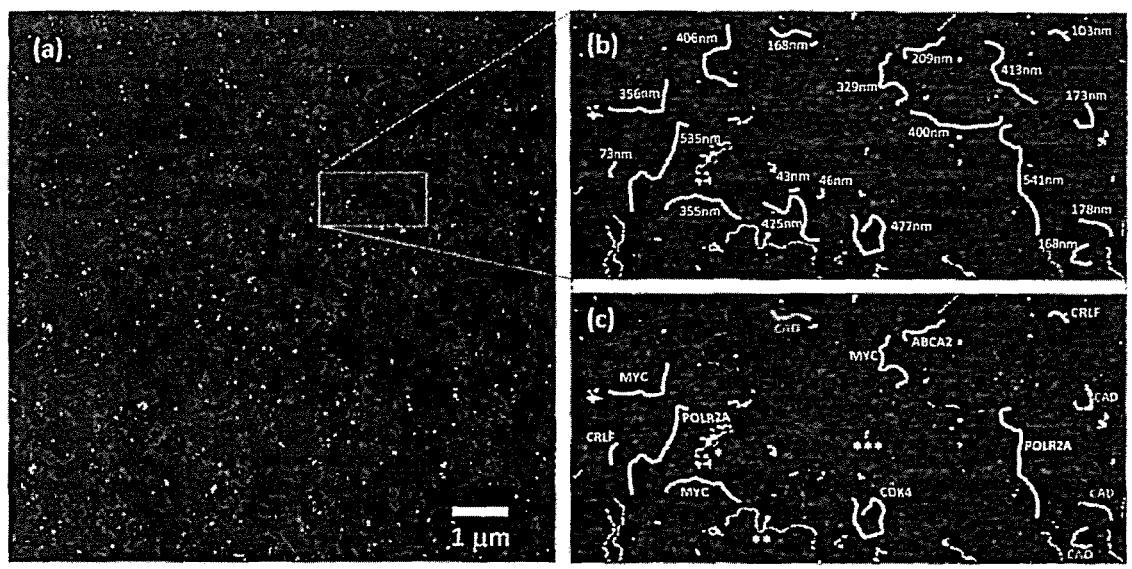
FIG. 3. (a) 10×10 μm AFM image of 10plex RT-PCR products (15 amplification cycles) produced using Universal Total Human Reference RNA as a template. (b) First inset shows various PCR amplicons highlighted in white with their associated backbone contour measurements. (c) Second inset shows individual amplicons classified by species. Note background objects not identified as amplicons due to their non-linear shape (* and ), or because they were shorter than the smallest expected amplicon (*).

We used APS-treated mica surfaces to bind DNA molecules for AFM imaging (Shlyakhtenko et al., 2003). Note that we did not purify mRNA from total RNA and used oligo(dT) reverse transcription primers for simplicity, so the solution after PCR contains, in addition to amplicons, genomic DNA contamination, rRNA, all mRNAs and cDNAs. However, as it can be seen on AFM image depicted on FIG. 3, the most abundant species on the mica surface are amplicon molecules, distinguishable from the other reaction constituents by length, height and persistent length.

Figure 4:
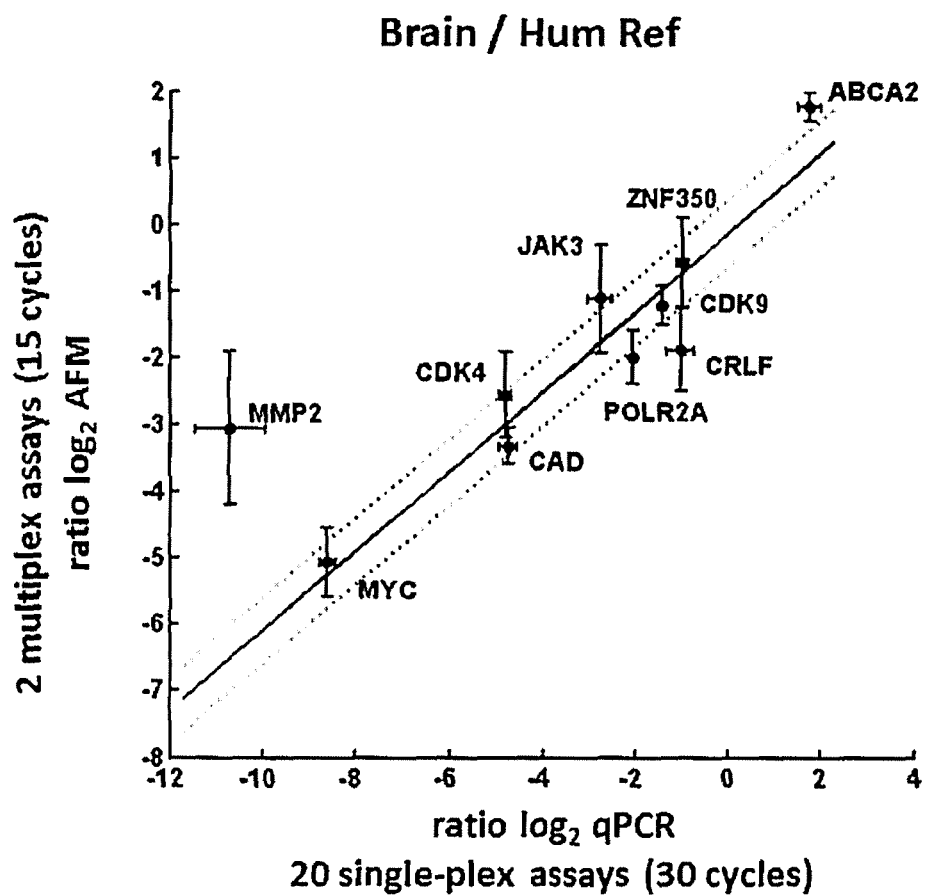
FIG. 4. Relative expression of target mRNAs in brain vs. human reference total RNA. The relative abundance of each target is determined by AFM (y-axis) vs. qPCR (x-axis). Error bars represent the estimated standard error of measurement for qPCR and PCR+AFM. The robust linear least squares fit is indicated by the solid black line, y=-0.14+0.60x, and the dotted black lines represent +/-0.5 $\log_2$ from the fit. The linear model fits the data well (R-squared of the fit is 0.87), indicating that the AFM data is a good predictor of the qPCR measurements. Dispersion of the data about the fit vs qPCR, given by the root mean squared error (RMSE), is 0.87 $\log_2$ units. Note that MMP2 is the only gene where the difference in Ct value for Human Reference and Brain sample is more than 10 $\log_2$ units at 60 C (see Table 1). This fact can indicate on the limits of dynamic range for AFM-based PCR using 1,000-2,000 molecules; increasing of the number of analyzed molecules will improve the dynamic range at the expense of throughput.

Using PCR/AFM we were able to reliably detect amplicons after 15 cycles (FIG. 4), which is lower than qPCR Ct values at comparable amounts of initial cDNA (see qPCR data in Table 1). In fact, there is a balance in choosing the number of PCR cycles: too few may result in decreased specificity and insufficient amount of amplicons, while too many will distort the initial distribution of nucleic acid targets, so the number of cycles is optimized for each assay. Methods of general PCR optimization are known in the art and involve changing the temperatures of the reaction and the concentrations of the component chemicals.

Here we used unmodified primers and amplicons. Labeling of primers at their 5'-end with AFM-detectable labels, such as streptavaidin or other proteins, or nanoparticles, can increase the level of multiplexing at least by a factor of two-fold (20 targets). Previously we have shown that sequence-specific labeling can be used to identify individual transcripts in a complex mixture containing several thousand distinct species (Reed et al., 2012). Sequence-specific labeling of amplicons could not only increase the level of multiplexing, but also allow for detection of genetic variations within the amplicons in cases where the amplicon length is detectably altered. In order to minimize the number of steps of our protocol, we used total RNA without enzymatic digestion of remaining genomic DNA and purification of mRNA. Although silica column-based purification allows for specific purification of dsDNA amplicons and elimination of almost all of ssRNA and ssDNA, the elution volume for a typical column is 6-10 microL. However, 0.1 microl or even less is required for deposition on the mica surface. Using advanced DNA purification techniques, such as purification by electric field (Kalyanasundaram et al., 2013; Zheng et al., 2004; Yeo et al., 2009; Kalyanasundaram et al., 2012), we can increase the sensitivity of this assay by 100×.

To determine the repeatability of the PCR+AFM measurement, we separately repeated the 10-plex measurements of Human Reference total RNA, de novo, in triplicate (see Table 2). The median coefficient of variation (standard error/mean) for the abundances of the ten targets was 0.25 (range 0.17-0.81). This compares to a median estimated lower limit of error due to statistical counting noise of 0.18 (range 0.05-0.38). The counting error is a function of the sampling depth (number of molecules counted per sample), and this type of error can be arbitrarily reduced by collecting more molecule counts at the expense of throughput. Note that qPCR itself has been shown to have a relative error (CV) in the range of 0.10-0.25 across most of its dynamic range (Ct values 18-30; the majority of our qPCR measurements had Ct values in this range). This data indicates that a 2-fold change in gene expression was detected in a single experiment in most cases where the total number of molecule counts per species is similar to that reported here.

TABLE 2

Technical repeats of AFM-determined molecule counts.

| Gene name | Universal Human 1 | Universal Human 2 | Universal Human 3 | Mean | σ | CV | $\sigma_{min}$ | $CV_{min}$ |
|---|---|---|---|---|---|---|---|---|
| ABCA2 | 56 | 56 | 85 | 66 | 14 | 0.22 | 8 | 0.12 |
| CAD | 264 | 292 | 374 | 311 | 42 | 0.14 | 14 | 0.04 |
| CDK4 | 30 | 38 | 10 | 27 | 15 | 0.56 | 5 | 0.19 |
| CDK9 | 38 | 62 | 35 | 45 | 12 | 0.26 | 7 | 0.14 |
| CRLF | 24 | 36 | 48 | 36 | 8 | 0.24 | 6 | 0.16 |
| JAK3 | 9 | 15 | 3 | 9 | 6 | 0.62 | 3 | 0.33 |
| MMP2 | 12 | 8 | 6 | 9 | 5 | 0.51 | 3 | 0.33 |
| MYC | 171 | 307 | 243 | 237 | 38 | 0.16 | 13 | 0.05 |
| POLR2A | 45 | 44 | 35 | 42 | 11 | 0.26 | 6 | 0.15 |
| ZNF350 | 12 | 16 | 11 | 13 | 2 | 0.19 | 4 | 0.27 |

Mean and standard deviations calculated after normalizing raw molecule counts such that the total number of corrected counts for each of the three samples are equal (normalizations: UH1 1.2, UH2 0.91, and UH3 0.94). Estimates of minimum variation due to statistical counting effects is calculated as the expected standard deviation of a binomial distribution: sqrt[counts * (1-p)] where p is sample fraction, given by counts per species/total molecules.

In this study, we restricted ourselves to gene expression profiling of ten genes. Undoubtedly this technique can be applied to virtually any genetic variation or a combination of genetic variations assayed in the same tube. While the slow imaging rate of our general purpose AFM was a practical constraint (~25 hr imaging time for 2 samples), if a commercially-available high scan rate AFM, had been used (e.g. Bruker FastScan or Asylum Cypher), the assay time would have been considerably reduced, e.g. to 1.4 hrs or less, which is of similar duration as regular 30-35 cycle qPCR, and significantly more rapid than existing hybridization-based detection schemes (14-16 hr) (Katagiri et al., 2009; Kulkarni et al., 2011). We note that automated sample handling and image analysis can be easily implemented using standard methods, as we and others have shown previously (Sundstrom et al., 2012; Fang et al., 1998), and that AFM technology has progressed to the point that image capture rates can approach that of optical microscopy (Kodera et al., 2011; Carberry et al., 2009; Picco et al., 2008; Hansma et al., 2006; Humphris et al., 2005).

While the invention has been described in its preferred embodiments, those of skill in the art will recognize the invention can be practiced with variations within the spirit and scope of the appended claims.

REFERENCES

Throughout this application, various references describe the state of the art to which this invention pertains. The disclosures of these references are hereby incorporated by reference into the present disclosure.

Bendall, S. C.; Nolan, G. P. *Nat Biotechnol* 2012, 30, 639-47.

Carberry, D. M.; Picco, L.; Dunton, P. G.; Miles, M. J. *Nanotechnology* 2009, 20, 434018 1-5.

Colman, H.; Zhang, L.; Sulman, E. P.; McDonald, J. M.; Shooshtari, N. L.; Rivera, A.; Popoff, S.; Nutt, C. L.; Louis, D. N.; Cairncross, J. G.; Gilbert, M. R.; Phillips, H.

S.; Mehta, M. P.; Chakravarti, A.; Pelloski, C. E.; Bhat, K.; Feuerstein, B. G.; Jenkins, R. B.; Aldape, K. *Neuro Oncol* 2010, 12, 49-57.

Cui, W.; Taub, D. D.; Gardner, K. *Nucleic Acids Res* 2007, 35, D805-809.

Dalerba, P.; Kalisky, T.; Sahoo, D.; Rajendran, P. S.; Rothenberg, M. E.; Leyrat, A. A.; Sim, S.; Okamoto, J.; Johnston, D. M.; Qian, D.; Zabala, M.; Bueno, J.; Neff, N. F.; Wang, J.; Shelton, A. A.; Visser, B.; Hisamori, S.; Shimono, Y.; van de Wetering, M.; Clevers, H.; Clarke, M. F.; Quake, S. R. *Nat Biotechnol* 2011, 29, 1120-7.

Eberwine, J.; Lovatt, D.; Buckley, P.; Dueck, H.; Francis, C.; Kim, T. K.; Lee, J.; Lee, M.; Miyashiro, K.; Morris, J.; Peritz, T.; Schochet, T.; Spaethling, J.; Sul, J. Y.; Kim, J. *J R Soc Interface* 2012, 9, 3165-83.

Fang, Y.; Spisz, T. S.; Wiltshire, T.; D'Costa, N. P.; Bankman, I. N.; Reeves, R. H.; Hoh, J. H. *Anal Chem* 1998, 70, 2123-9.

Garcia-Bilbao, A.; Armananzas, R.; Ispizua, Z.; Calvo, B.; Alonso-Varona, A.; Inza, I.; Larranaga, P.; Lopez-Vivanco, G.; Suarez-Merino, B.; Betanzos, M. *Bmc Cancer* 2012, 12, 43 1-13.

Habel, L. A.; Shak, S.; Jacobs, M. K.; Capra, A.; Alexander, C.; Pho, M.; Baker, J.; Walker, M.; Watson, D.; Hackett, J.; Blick, N. T.; Greenberg, D.; Fehrenbacher, L.; Langholz, B.; Quesenberry, C. P. *Breast Cancer Res* 2006, 8, R25 1-15.

Hansma, P. K.; Schitter, G.; Fantner, G. E.; Prater, C. *Science* 2006, 314, 601-2.

Humphris, A. D. L.; Miles, M. J.; Hobbs, J. K. *Appl Phys Lett* 2005, 86, 043106 1-3.

Kalyanasundaram, D.; Inoue, S.; Kim, J. H.; Lee, H. B.; Kawabata, Z.; Yeo, W. H.; Cangelosi, G. A.; Oh, K.; Gao, D.; Lee, K. H.; Chung, J. H. *Microfluidics and Nanofluidics* 2012, 13, 217-225.

Kalyanasundaram, D.; Kim, J. H.; Fotouhi, G.; Lee, H. B.; Hiraiwa, M.; Oh, K.; Lee, K. H.; Chung, J. H. *Analyst* 2013, 138, 3135-8.

Katagiri, F.; Glazebrook, J. *Curr Protoc Mol Bio* 2009, 85:22.4.1-22.4.13.

Kodera, N.; Yamamoto, D.; Ishikawa, R.; Ando, T. *Nature* 2011, 468, 72-76.

Kulkarni, M. M. *Curr Protoc Mol Bio* 2011, 25B.10.1-25B.10.17.

Mizuarai, S.; Irie, H.; Kotani, H. *Curr Mol Med* 2010, 10, 596-607.

Nagalakshmi, U.; Waern, K.; Snyder, M. *Curr Protoc Mol Biol* 2010, Chapter 4, Unit 4 11 1-13

Picco, L. M.; Dunton, P. G.; Ulcinas, A.; Engledew, D. J.; Hoshi, O.; Ushiki, T.; Miles, M. J. *Nanotechnology* 2008, 19, 384018 1-6.

Powell, A. A.; Talasaz, A. H.; Zhang, H.; Coram, M. A.; Reddy, A.; Deng, G.; Telli, M. L.; Advani, R. H.; Carlson, R. W.; Mollick, J. A.; Sheth, S.; Kurian, A. W.; Ford, J. M.; Stockdale, F. E.; Quake, S. R.; Pease, R. F.; Mindrinos, M. N.; Bhanot, G.; Dairkee, S. H.; Davis, R. W.; Jeffrey, S. S. *Plos One* 2012, 7, e33788.

Reed, J.; Hsueh, C.; Lam, M. L.; Kjolby, R.; Sundstrom, A.; Mishra, B.; Gimzewski, J. K. *J R Soc Interface* 2012, 9, 2341-50.

Sanchez-Freire, V.; Ebert, A. D.; Kalisky, T.; Quake, S. R.; Wu, J. C. *Nat Protoc* 2012, 7, 829-38.

SantaLucia, J., Jr. *Methods Mol Biol* 2007, 402, 3-34.

Shlyakhtenko, L. S.; Gall, A. A.; Filonov, A.; Cerovac, Z.; Lushnikov, A.; Lyubchenko, Y. L. *Ultramicroscopy* 2003, 97, 279-287.

Stahlberg, A.; Kubista, M.; Aman, P. *Expert Rev Mol Diagn* 2011, 11, 735-40.

Sundstrom, A.; Cirrone, S.; Paxia, S.; Hsueh, C.; Kjolby, R.; Gimzewski, J. K.; Reed, J.; Mishra, B. *IEEE Trans Inf Technol Biomed* 2012, 16, 1200-7.

Ye, J.; Coulouris, G.; Zaretskaya, I.; Cutcutache, I.; Rozen, S.; Madden, T. L. *BMC Bioinformatics* 2012, 13, 134.

Yeo, W. H.; Chung, J. H.; Liu, Y.; Lee, K. H. *J Phys Chem B* 2009, 113, 10849-58.

Zheng, L.; Brody, J. P.; Burke, P. J. *Biosens Bioelectron* 2004, 20, 606-19.

The invention claimed is:

1. A method for analyzing a plurality of multiple nucleic acid targets in a complex mixture, comprising the steps of
   performing a multiplex polymerase chain reaction (PCR) using primers which produce a uniquely sized amplicon for each of said targets, wherein said primers are added together in a single solution with said complex mixture;
   identifying individual amplicons using atomic force microscopy (AFM);
   correlating identified amplicons with specific nucleic acid targets of said multiple nucleic acid targets, wherein said identifying and correlating steps allow quantification of said individual amplicons, and thereby
   quantifying said specific nucleic acid targets in said complex mixture as a function of a total number of each individual amplicon identified.

2. The method according to claim 1, wherein cycling parameters of said multiplex PCR includes no more than 10 to 15 thermal cycles.

3. The method according to claim 1, wherein said uniquely sized amplicons are longer than 100 base pairs and have at least 100 base pairs differences in size.

4. The method according to claim 1, further comprising a step of visualizing said uniquely sized amplicons on an agarose gel.

5. The method according to claim 1, wherein said AFM has a high scan speed with an imaging rate of 1 frame per second or faster, greater than 1 million pixels per second, and pixel sizes of 2×2 nm up to 100×100 nm.

6. The method of claim 1, wherein each of said primers is at a concentration less than or equal to 200 nM.

* * * * *